United States Patent [19]

McDougall

[11] Patent Number: 5,625,916
[45] Date of Patent: May 6, 1997

[54] TOOTHBRUSH

[76] Inventor: Greg McDougall, 5C, Taichi Court, 132 Austin Road, Tsimshatsui, Kowloon, Hong Kong

[21] Appl. No.: 449,298
[22] Filed: May 24, 1995
[51] Int. Cl.$^6$ .................... A61C 17/34; A46B 13/02
[52] U.S. Cl. .................................. 15/28; 15/22.1
[58] Field of Search .................... 15/22.1, 22.4, 15/28, 29

[56] References Cited

U.S. PATENT DOCUMENTS

| | | | |
|---|---|---|---|
| 1,255,028 | 1/1918 | Leonard et al. | 15/22.1 |
| 2,379,049 | 6/1945 | Tompkins | 15/22.1 |
| 4,479,516 | 10/1984 | Hunter | 15/28 |
| 5,416,942 | 5/1995 | Baldacci et al. | 15/28 |

Primary Examiner—Mark Spisich
Attorney, Agent, or Firm—Gunn, Lee & Miller, P.C.

[57] ABSTRACT

An electrical driven toothbrush has a rotatable shaft with a remote end which fits into a slot in a bristle holder. The holder is mounted for rotation on a post supported by a head. When the shaft rotates the remote end describes a circle and driving engages the slot to cause the holder to vibrate.

4 Claims, 2 Drawing Sheets

TOOTHBRUSH

BACKGROUND OF THE INVENTION

Field of the Invention

The invention relates to toothbrushes,

Description of the Prior Art

The invention relates more particularly to electrically driven toothbrushes in which brush bristles are arranged to be moved relative to the toothbrush handle.

There are many examples of such toothbrushes including the disclosure in 1939 of rotary driven bristles in U.S. Pat. No. 2215031, A similar rotational drive arrangement is also shown in U.S. Pat. No. 4845795, U.S. Pat. No. 4156620 explains how a rotational motor drive is converted into reciprocal linear motion to drive the bristles rotationally clockwise and counterclockwise, U.S. Pat. No. 3577579 discloses a toothbrush in which a toothbrush head is moved in relation to a brush holder so that all the bristles mounted in the brush head move together sideways and backwards and forwards relative to the holder.

SUMMARY OF THE INVENTION

The present invention is concerned with moving bristles relative to a toothbrush head to enhance the cleaning action of toothbrushes in use and has as an object to provide toothbrushes in which relative motion is achieved in a simple and effective manner.

According to the invention there is provided an electrical driven toothbrush having a handle, a head, a rotatable shaft having a longitudinal central axis extending from the handle to the head, and a bristle holder pivotably mounted to the head and drivingly engaged by a remote end of the shaft which is off-center with respect to the central axis so that the brush holder vibrates about its pivot when the shaft rotates.

The shaft is preferably integrally formed and its remote end is bent away from the central axis.

The bristle holder may have a slot into which the remote end of the shaft fits.

The bristle holder may be mounted to rotate about an axis.

The bristle holder may be arranged to vibrate through an angle between 10° and 50°; preferably the angle is approximately 30°.

BRIEF DESCRIPTION OF THE DRAWINGS

A toothbrush according to the invention will now be described by way of example with reference to the accompanying drawings in which.

DESCRIPTION OF THE PREFERRED EMBODIMENTS

Figure 1:
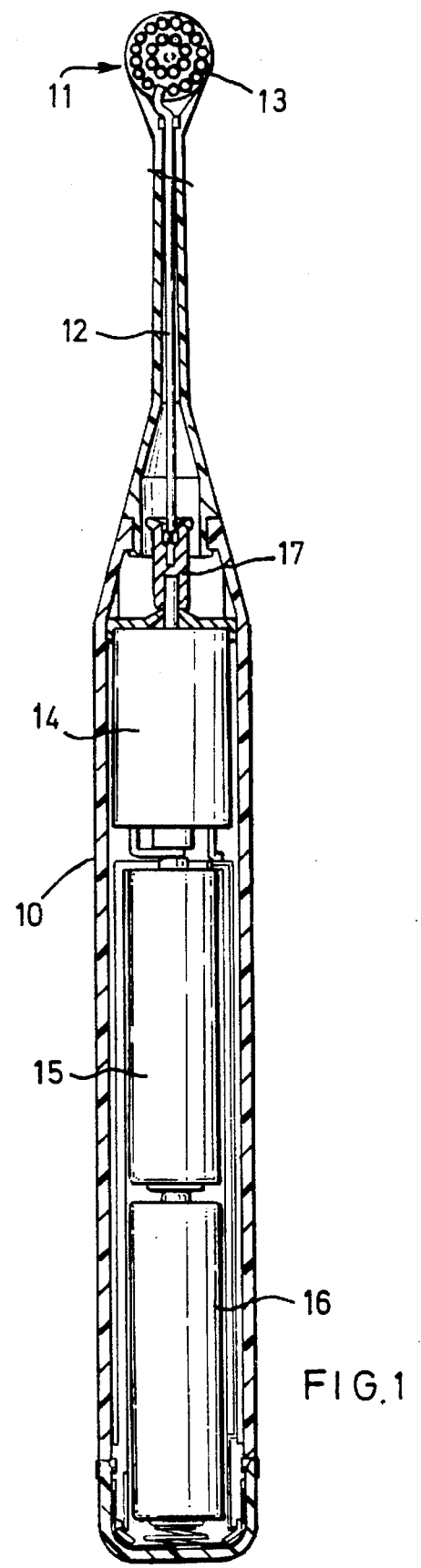
FIG. 1 is a sectional bottom view of the toothbrush.
Figure 4:
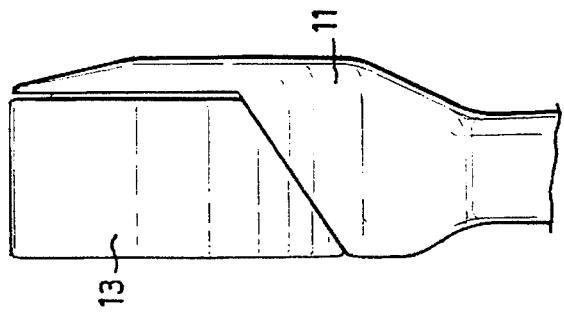
FIG. 4 is an opposite side view of FIG. 2.
Figure 7:
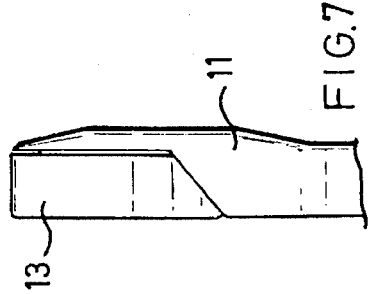
FIGS. 5, 6 and 7 are respectively the same views as FIGS. 2, 3 and 4 of a different toothbrush and to a different scale.

Referring to the drawings, in FIG. 1 the toothbrush comprises a handle portion 10 at a first end of the toothbrush, a head section 11 at a second end of the toothbrush, a rotatable shaft 12 extending from the handle to the head, and a generally circular bristle holder 13. The handle provides compartments for holding an electric motor 14 and two batteries 15 and 16. A shaft coupling 17 is arranged to grip one end of the shaft 12 and allow the shaft to be pulled out for cleaning or replacement as will be described below.

Figure 2:
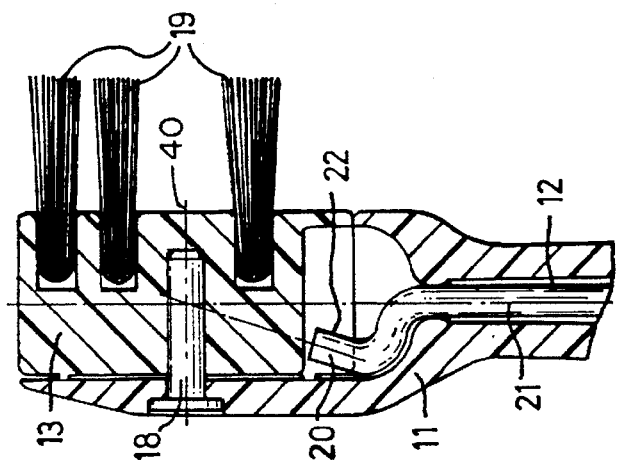
FIG. 2 shows a cross-sectional side view of part of the toothbrush.

The head 11, as is better seen in FIG. 2, supports a post 18 which provides a rotational pivot axis for the bristle holder 13. Bristles 19 are shown for illustrative purposes only in FIG. 2. The shaft 12 has an integrally formed remote-most end 20 that is off-set from a central longitudinal axis 21 of the shaft.

The remote-most end 20 fits into a slot 22 (see FIG. 3) formed in a side of the bristle holder 13. It will be noted that the end 20 points towards an intersection of the first axis 21 and a second central axis 40 of the post 18. When the shaft 12 is rotated by the motor 14, the remote end 20 describes a circle about the shaft 12 and drivingly engages the slot 22 to cause the bristle holder 13 to vibrate. As may be seen in FIG. 3, slot 22 is closed-ended and extends radially inward from the outer circumference of the holder to less than the distance to the center of the holder and between adjacent pairs of bristle holes. Thus, the holder 13 pivots or rotates forwards and backwards about the center of the post 18. Such vibrations comprise the relative motion between the head 11 and the bristles 19 and is generally beneficial for efficient cleaning of teeth. The width of the slot 22 is preferably generally the same as the diameter of the end 20 to leave minimum play; this keeps noise to a minimum in use.

Preferably, the motor 14 runs at around 6000 rpm. Where desired, the motor can run at other speeds or be arranged to run at two or more speeds selectable by the user.

Figure 5:
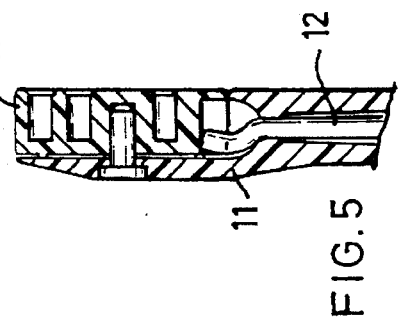

FIG. 1 shows a toothbrush where the holder 13 vibrates or rotates through an angle of 30°. In FIG. 2, the angle is 35° and in FIG. 5 the angle is 15°. It will therefore be appreciated that the rotational angle can be chosen by fitting different shafts 12 and that the same bristle holder can be used for all angles.

Figure 3:
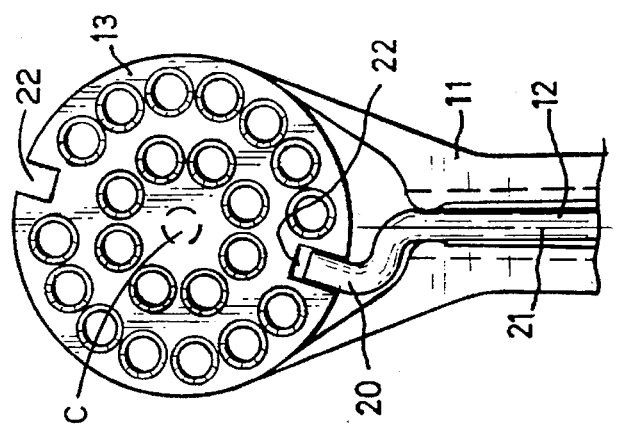
FIG. 3 is a sectional bottom view of FIG. 2.
Figure 6:
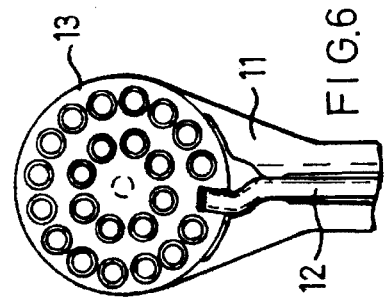

Each bristle holder 13 may be provided with more than one slot 22 as may be seen in FIG. 3, opposite each other so as to be better balanced or so that different slots can be used if the one slot wears or if the bristles wear unevenly in use. In other words, the holder 13 can then be set up in two or more rotational positions. The holder 13 is preferable easily removable from the head 11, by being spring clipped to the post 18 for example. Such removal allows better cleaning and storing in a hygienic container perhaps and also enables the shaft 12 to be readily withdrawn and replaced when required.

The described shafts 12 are preferably integrally formed, i.e., a single length of a thin rod and shaped as shown. However, it is possible to arrange for the remote end 20 to be separately formed or provided and fixed to a straight end part of the shaft. Such a separate part can be a brush having a central axis coinciding with the axis 21 of the shaft and an off-center driving post. The driving post then takes up the position and function of the remote end 20. Thus, the driving post and the slot 22 then form the driving engagement between the shaft and the holder 13 and so the driving post can be regarded as the remote end of the shaft.

It is also possible, but not usually so convenient, in some embodiments of the invention to arrange for the holder 13 to be hingedly pivoted at one side, for example opposite the shaft. In such a case, bristles mounted nearer the hinged pivot will not actually move as much as bristles at the side next to the shaft but they will still vibrate significantly.

It will also be appreciated that whether pivoted to rotate or to hinge, the bristle holder 13 need not be circular. However, a circular holder 13 is normally preferred so that its rotational position can be changed when desired, as mentioned above.

I claim:

1. An electrically driven toothbrush comprising:

a handle portion at a first end of said toothbrush;

a head section at a second end of said toothbrush;

a rotatable, integrally formed shaft extending from said handle portion to said head section and having a first longitudinal central axis; and a generally circular, bristle holder pivotally mounted to said head section on a post having a second longitudinal axis and drivingly engaged by a remote-most end of said shaft, said remote-most end of said shaft bent toward an intersection of said first longitudinal central axis and said second longitudinal axis, said bristle holder having a first closed-ended slot extending radially inward from the outer circumference of said holder to less than the distance to the center of said holder to receive and retain said remote-most end of said shaft, said bristle holder having a plurality of bristle receiving and retaining holes formed in and distributed around a top surface of said holder, said slot extending inwardly between an adjacent pair of said holes.

2. An electrical driven toothbrush according to claim 1, in which the bristle holder is arranged to vibrate through an angle between 10° and 50°.

3. An electrical driven toothbrush according to claim 2, in which the angle is approximately 30°.

4. A toothbrush according to claim 1 further comprising a second closed-ended slot extending radially inward from said outer circumference of said holder to less than the distance to the center of said holder, said second closed-ended slot opposite said first closed-ended slot.

* * * * *